United States Patent [19]
Gould

[11] Patent Number: 5,546,943
[45] Date of Patent: Aug. 20, 1996

[54] STIMULATING A BENEFICIAL HUMAN RESPONSE BY USING VISUALIZATION OF MEDICAL SCAN DATA TO ACHIEVE PSYCHONEUROIMMUNOLOGICAL VIRTUAL REALITY

[76] Inventor: Duncan K. Gould, 747 Calmar Ave., Oakland, Calif. 94610

[21] Appl. No.: 353,140

[22] Filed: Dec. 9, 1994

[51] Int. Cl.⁶ ........................................... A61B 6/00
[52] U.S. Cl. ..................... 128/653.1; 128/653.2; 128/898; 364/413.13; 364/413.22; 434/262; 434/267
[58] Field of Search .............. 128/653.1, 653.2, 128/898; 364/413.02, 413.13, 413.22; 434/262, 267

[56] References Cited

PUBLICATIONS

Moyers, Bill, "Healing and The Mind" pp. 195–211, 1993.

*Primary Examiner*—Ruth S. Smith
*Attorney, Agent, or Firm*—Charles J. Kulas; Philip H. Albert; Townsend and Townsend and Crew LLP

[57] ABSTRACT

A visualization system using a computer to provide a patient with a view of their internal anatomy based on medical scan data. The medical scan data is obtained from three-dimensional scanning system, such as Magnetic Resonance Imagery (MRI), Computer-Aided Tomography (CAT), Positron Emission Tomography (PET) and Nuclear Magnetic Resonance (NMR). The patient is presented with such data in an interactive virtual reality environment. The patient acts upon indications of the ailment within the virtual reality environment by using "tools" or other devices that produce a visual representation of the ailment being diminished in nature. This creates a psychoneuroimmunological response in the patient which aids the patient in combatting and recovering from the disease. Embodiments of the invention enhance the PNI response by providing more numerous and realistic sensory input in the form of, e.g., three-dimensional audio and high resolution volume rendering and animation.

16 Claims, 6 Drawing Sheets

STIMULATING A BENEFICIAL HUMAN RESPONSE BY USING VISUALIZATION OF MEDICAL SCAN DATA TO ACHIEVE PSYCHONEUROIMMUNOLOGICAL VIRTUAL REALITY

BACKGROUND OF THE INVENTION

This invention relates generally to improving the treatment of medical patients and specifically to producing a beneficial response in a patient by using a computer system to enable the patient to visualize and perform actions upon a representation of their ailment or other physiological manifestation.

Today, advanced medical instruments are able to perform relatively noninvasive scans of a patient's internal organs so that physicians and technicians may "see" the patient's dysfunctioning organ, disease, injury, mental condition, etc. Examples of scanning instruments are Magnetic Resonance Imaging (MRI), Computer-Aided Tomography (CAT), Positron Emission Tomography (PET) and Nuclear Magnetic Resonance (NMR). These techniques employ sophisticated instruments to obtain scan data of the patient's internal anatomy. The scan data is used to generate a visual representation of the areas of interest within the patient's body so that diagnosis and presurgical planning, or other treatment, may be more accurately performed.

Although the scanning instruments used in obtaining scan data are noninvasive (i.e., they do not involve surgical procedures) the operation and maintenance of such instruments is expensive and elaborate, often requiring various support equipment and teams of specialists. The instruments are often a scarce resource and the cost of obtaining a scan is expensive. Moreover, some scans are limited in the number of times they can be performed, such as when testing occurs over a relatively short period, and some scans can be performed only a limited number of times within the patient's lifetime. Because of these factors the scan data represents very valuable, sometimes irreplaceable, data.

The scan data is typically used only once or a few times to display a three-dimensional visual representation of the patient's internal anatomy for a physician or diagnostician. For example, a CAT scan of a patient's lung may be used to display the internal lung tissue in order for a physician to detect the presence of a cancer tumor which would be undetectable by other diagnostic methods, such as an X-ray. The use of two or more sets of scan data from different techniques (e.g., a CAT scan and a PET scan) may be used to provide an improved display of a patient's ailment since each system is attuned to detecting different characteristics.

Traditionally, the scan data is displayed on a device such as a cathode ray tube (CRT) under the direction of the diagnostician. The diagnostician can, for example, manipulate the viewpoint of the three-dimensional image of the patient's internal organs so that the display may be changed to show different "layers" of a patient's organ as, for example, where layers of tissue are "removed" from an organ to show the organ's interior at increasing depth (i.e., "classification," the peeling away of layers of tissue to show what is underneath). The diagnostician can also manipulate the viewpoint to move around the organ, as needed, for ease of viewing the internal organs and for identifying and observing the patient's disorder.

Improvements in visualization technology allow a diagnostician to have a highly detailed and realistic three-dimensional view of a patient's internal anatomy as represented by the scan data. For example, the diagnostician may view the data in a stereo perspective view. Through the use of very fast computers, or multiple computers, the realism and detail of such three-dimensional displays is continually improving.

However, even with the existence of the noninvasive scanning technology and advanced visualization capabilities modern medicine still encounters many problems in treating persistent and tragically debilitating diseases. Examples of such diseases are Acquired Immune Deficiency Syndrome (AIDS) and cancer. Even though advances in scanning and visualization technology allow more accurate diagnoses and are helpful in planning surgical procedures or other treatments, they are of little use in directly treating the disease. That is, modern medicine is still reduced to surgical, chemical, radiation, or other therapies which often serve only to delay the progress of the disease, often at the expense of the greater part of the patient's health and quality of life. Moreover, the helplessness that a patient feels at being victimized by both the disease and the treatment may further aggravate the effects of the disease on the patient.

Thus, it is desirable to produce an invention which will apply the advancements in scanning systems and visualization technology not only to diagnose, but to treat the patient's ailment. It is also desirable to utilize valuable scan data as much as possible to assist in the patient's recovery. Furthermore, it is desirable to empower the patients and to enable them to take action against their ailments to produce beneficial emotional and physical responses in the patients.

SUMMARY OF THE INVENTION

The present invention provides a method and apparatus for stimulating a beneficial response in the patient. The patient is able to view their internal anatomy as represented by medical scan data in a virtual reality environment. Moreover, the patient is able to use "tools" to act upon, correct, eradicate, or otherwise reduce the effect of their ailment by interacting with a visualization of the ailment. The interaction results in visual animations that show an instant beneficial result of the patient's actions.

One embodiment of the invention allows a patient to visually enter their internal anatomy, locate the ailment, and attack it with a selection of tools that produce a visualization of the ailment being eradicated. This action and viewing stimulates the psychoneuroimmunological (PNI) response in the patient. Such a response has been shown to provide a beneficial effect on the patient's recovery. The PNI response is further enhanced by making the experience as "real" as possible for the patient. In further embodiments of the invention the PNI response is intensified through use of three-dimensional sound, advanced input devices such as a data glove, biofeedback motivators, a color tagging scheme and other visual, aural and sensory effects under the control of a computer to produce a heightened mental and physical awareness of the patient's eradication of their ailment.

In one embodiment, a method for stimulating a beneficial response in a patient with an ailment is employed. The method uses a computer system. The computer system includes a processor coupled to a user input device, memory, and output device. The method comprises the steps of obtaining medical scan data from the patient's anatomy wherein the medical scan data includes an indication of the ailment; inputing the medical scan data into the computer system; displaying to the patient a visual representation of at least a portion of the medical scan data on the output device, wherein the displayed portion includes a depiction of the ailment; accepting signals from the user input device, wherein the accepted signals indicate a patient's action on the visual representations; and modifying the visual representation to suggest a diminishing of the ailment so that a beneficial response is stimulated in the patient.

DETAILED DESCRIPTION OF A PREFERRED EMBODIMENT

Figure 1:
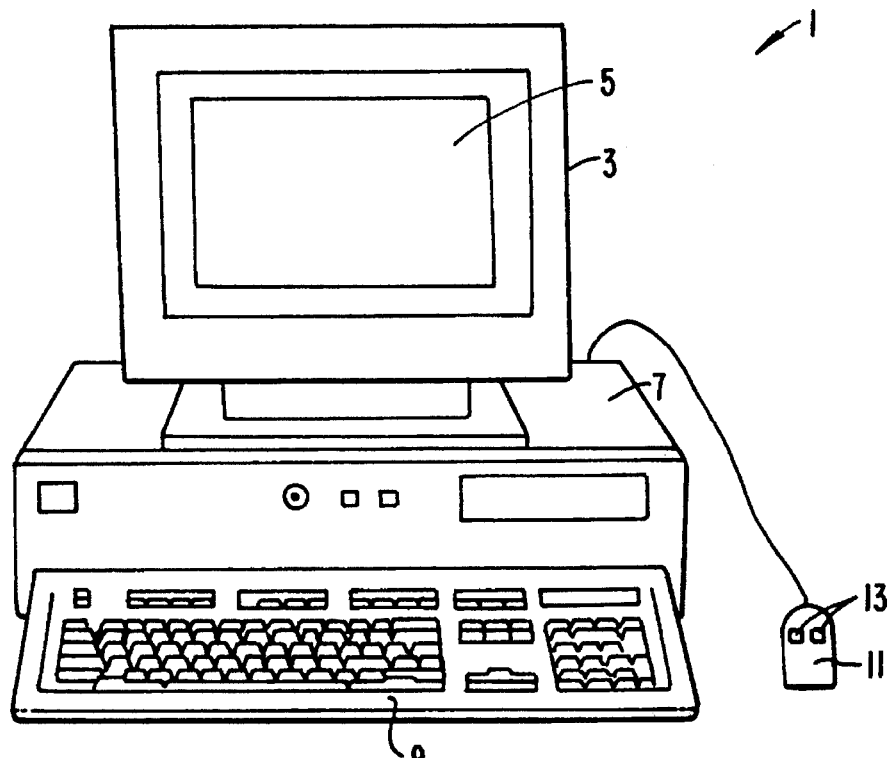
FIG. 1 is an illustration of a computer system suitable for use with the present invention.

A preferred embodiment employs several computer systems interconnected by various buses, as described below. FIG. 1 is representative of a small computer system that can be used to implement the portable or network versions of the invention as discussed below. FIG. 1 shows computer system 1 including display device 3, display screen 5, cabinet 7, keyboard 9 and mouse 11. Mouse 11 and keyboard 9 are "user input devices." Other examples of user input devices are a touch screen, light pen, track ball, data glove, etc.

Mouse 11 may have one or more buttons such as buttons 13 shown in FIG. 1. Cabinet 7 houses familiar computer components such as disk drives, a processor, storage device, etc. As used in this specification "storage device" includes any storage mechanism used in connection with a computer system such as disk drives, magnetic tape, solid state memory, bubble memory, etc. Cabinet 7 may include additional hardware such as input/output (I/O) interface cards for connecting computer system 1 to external devices such as an optical character reader, external storage devices, other computers or additional devices.

Figure 2:
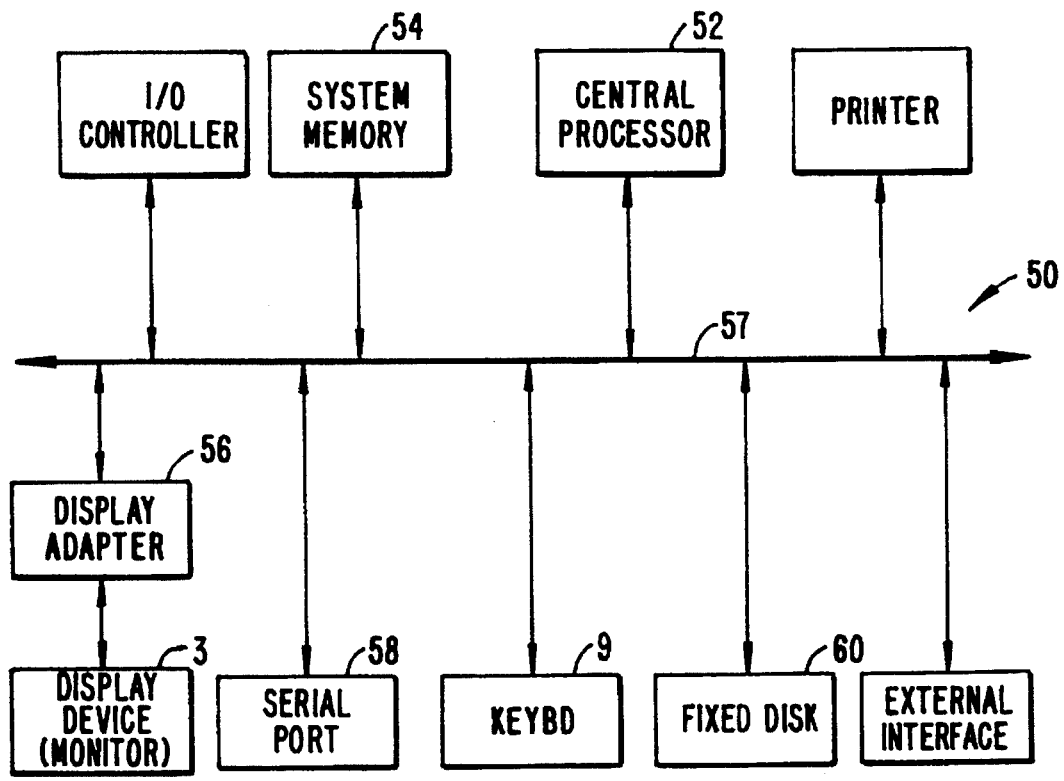
FIG. 2 is an illustration of basic subsystems in the computer system of FIG. 1.

FIG. 2 is an illustration of basic subsystems in computer system 1 of FIG. 1. In FIG. 2, subsystems are represented by blocks such as central processor 52, system memory 54, display adapter 56, (monitor) display device 3, etc. The subsystems are interconnected via a system bus 57. Additional subsystems such as a printer, keyboard, fixed disk, etc., are shown. Peripherals and input/output (I/O) devices can be connected to the computer system by, for example, serial port 58. Serial port 58 can be used to connect the computer system to a modem or mouse input device. The interconnection via system bus 57 allows central processor 52 to communicate with each subsystem and to control the execution of instructions from system memory 54 or fixed disk 60, and the exchange of information between subsystems. Other arrangements of subsystems and interconnections are possible.

FIGS. 1 and 2 are examples of the type of housing and basic subsystems found in small or medium computers. Larger computer systems, sometimes referred to as main- frames, will house essentially the same components as those in the computer of FIGS. 1 and 2, except that the components will be larger in number, of greater capacity or of increased speed. It will be apparent to one of skill in the art that computer systems suitable for use with the present invention are many and varied. A preferred embodiment of the present invention uses multiple computers systems as shown in FIG. 3.

System Overview

Figure 3:
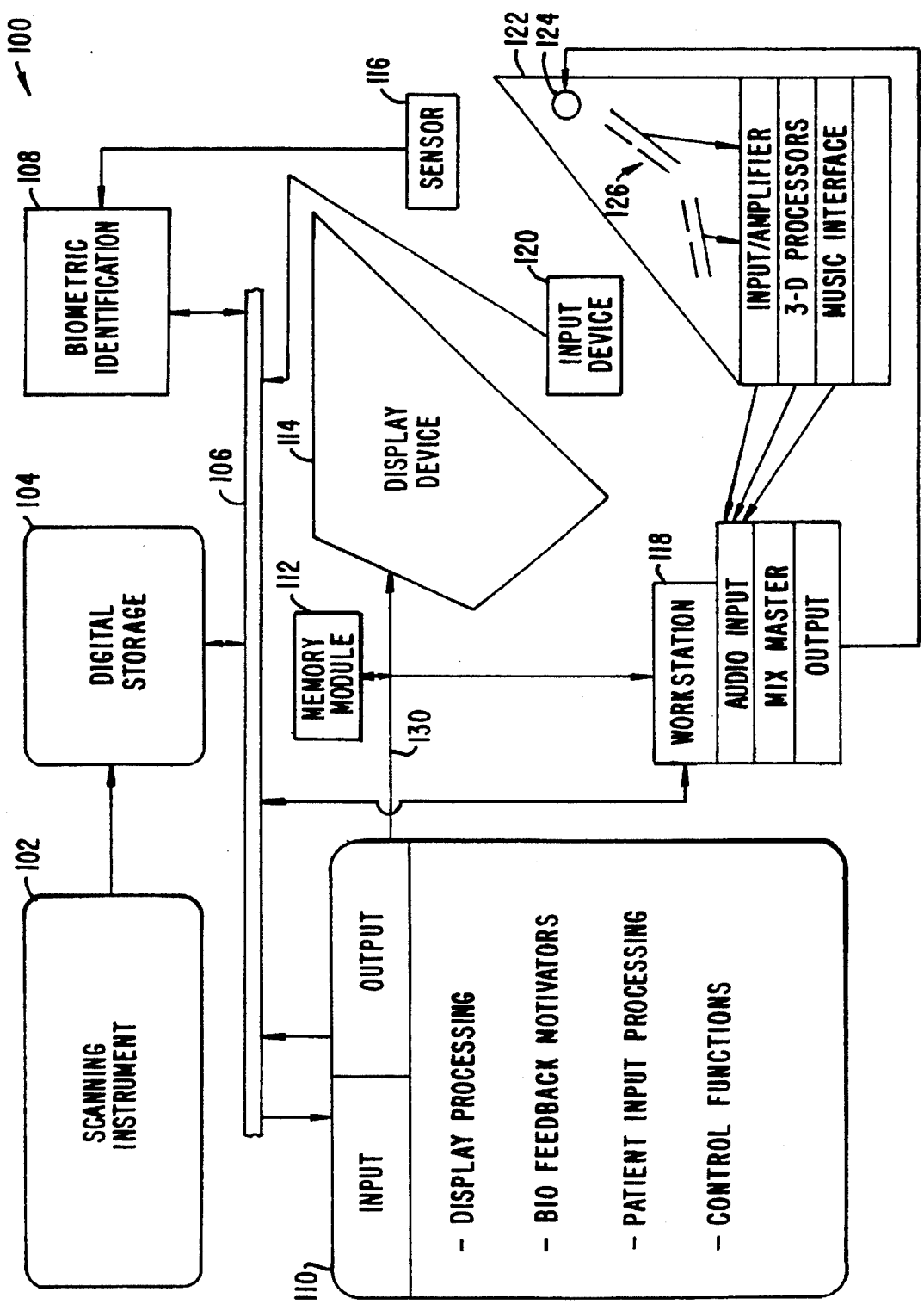
FIG. 3 is a system diagram of a preferred embodiment of the present invention.

FIG. 3 is a system diagram of a preferred embodiment of the present invention. In FIG. 3, hardware components of the system are shown as boxes interconnected by lines representing, e.g., hardwire, optical fiber, infrared, radio transmission, or other forms of communication between the hardware components.

In FIG. 3, system 100 includes scanning instrument 102. Scanning instrument 102 may be any instrument or method for obtaining medical data about a patient's anatomy such that the data can be used to construct a model of the patient's internal anatomy and display a representation of the model to the patient. Examples of such instruments are the MRI, CAT, PET and NMR instruments discussed above. Other instruments or data sources may be used. In one embodiment the scan data from instrument 102 is obtained at some time prior to a patient's session with system 100. However, with advances in technology it will be possible to provide virtually instantaneous data obtained and processed from the patient in real time so that the patient may view a model of their internal anatomy based on scan data obtained just moments prior to the viewing. Another advantage of using real time scan data is that patients can immediately see physiological changes in their bodies due to the visualization experience or other factors.

Even with scan data obtained minutes, hours or days before the patient uses the system, the system can provide beneficial results. This is because the changes in the patient's internal anatomy due to the onset and progress of a disease usually occur relatively slowly. A distinct feature of the present invention is that the scan data is data that is routinely obtained as part of the process of diagnosing and treating a typical patient. Although the cost of independently obtaining such scan data could be enormous, the patient's use of the present invention in conjunction with the diagnostic and treatment process creates no additional costs. In fact, in current practice, the scan data is usually viewed only once or a few times by a diagnostician and then never used again. The present invention provides for continued beneficial use of valuable scan data that would otherwise be discarded.

Scanning instrument 102 transfers the scan data to digital storage 104. In a preferred embodiment, the data is converted into a form more suitable for display, such as a volumetric dataset or other three-dimensional data form. Digital storage 104 may be any mass storage device such as a redundant array of inexpensive devices (RAID), large RAM, streaming tape, bubble memory, optical media, or other form of digital storage.

While FIG. 3 shows system 100 as a single large system permanently installed at a central hospital, for example, other embodiments of the invention allow the data in digital storage 104 to be accessed by other computers. These other computers may be at the patient's home, in another hospital or in some other location. By allowing the patient to remotely access their three-dimensional data, for example, by "dialing in" via a telephone line to download the data, the patient can use the invention in a limited, but more convenient, fashion. This allows for home sessions of the invention to be conducted while the patient's session is monitored from another location, such as the hospital where the full system, including digital storage 104, is located. A home television could also be used as the display device, especially when interactive television technology becomes commonplace permitting data to be transmitted in both directions over television cable lines or fiber optic cables.

Moreover, the patient's personal data may be stored in a device that is small enough to be easily portable. Such a device could be a RAM card, for example, or a portable disk drive. The portable device could then be transported to another location where there is a full system such as the system of FIG. 3, or a smaller computer system, such as the system of FIG. 1.

Naturally, smaller systems such as the computer system of FIG. 1, or a portable "laptop" computer system, will not provide the full effect of virtual reality since the display is limited to a small rectangular screen, and other hardware, such as the patient chair, discussed below, will be missing. However, the patient will still receive a benefit in being able to visualize and act upon the medical scan data to the extent that the smaller and portable computer systems permit. In a preferred embodiment, a smaller or relatively portable computer system suitable for use with the present invention is the Silicon Graphics Indy computer, manufactured by Silicon Graphics, Inc. of Mountain View, Calif.

Digital storage 104 is connected to bus 106 for transfer of the three-dimensional data to mainframe computer 110. Mainframe computer 110 includes input and output processing hardware and software for performing the major functions of display processing, biofeedback motivating, patient input processing and other control functions. In a preferred embodiment, mainframe computer 110 is a Silicon Graphics Onyx computer, manufactured by Silicon Graphics, Inc. of Mountain View, Calif. that can be configured with up to eight processors, as needed, to perform the advanced display processing and other functions in a parallel processing architecture.

Mainframe computer 110 communicates, via bus 106, with digital storage 104, biometric identification unit 108 and workstation 118. Workstation 118 is used by a supervisor to monitor and control, if necessary, the patient's interaction with the system. Workstation 118 is a medium- to small-scale computer such as that shown in FIG. 1. Workstation 118 performs some audio processing functions as shown in FIG. 3, such as accepting and processing audio input, mixing sound levels, outputting sound to speakers built into the patient's enclosure 122, etc. Workstation 118 also serves to accept supervisor inputs to control the operation of the system.

Audio input is received by workstation 118 from patient enclosure 122. Such input is obtained from microphones such as 126, located within the patient enclosure. This eliminates the need for sensors to be attached to the patient's body. Even the biofeedback sensors, discussed below, are implemented by using microphones that do not directly contact the patient's body but are built into the patient enclosure. The microphones are used to detect sounds emanating from the patient's body such as breathing, heartbeat, internal organs, etc. These sounds are then processed, amplified, and selectively presented to the patient along with music, if desired, via speakers such as speaker 124.

The use of the patient's own body sounds serves to enhance the patient's experience of being virtually present within their own body. This, in turn, intensifies the psychological and physical impact of the experience and leads to a heightened PNI response. The patient may choose the type of sounds played through the speakers. For example, the patient may desire birds or crickets chirping, the sound of ocean waves, classical music, etc. These sounds may be used in place of, or mixed together with, the sounds of the patient's own biology.

Patient enclosure 122 is similar to a standard flight simulator chair. Normally the patient will not be connected to any equipment other than normal contact with the chair back and handheld controls (e.g., pistol-grip joystick) for maneuvering the viewpoint through the patient's body. For disabled patients, different forms of the flight simulator chair can be used, such as providing tongue, chin, eye-activated, or other controls for paralyzed patients.

Another embodiment of the invention uses a "wet" patient enclosure. In the wet enclosure, the patient sits in a plastic chair in a round tub partially filled with water at a temperature of about 102° F. A preferred embodiment uses "ozonated" water as an added purifying agent. The water level comes midway up the patient's chest or to whatever level is comfortable. The patient sees the same large viewing screen that essentially fills the patient's field of view as in the "dry" patient enclosure discussed above. The same types of controls, such as a joystick, can be employed as in the "dry" enclosure. In the wet enclosure the patient may wear a headset to hear the audio portion of the presentation or a suitable system for conveying the sound by external speakers may be employed.

Returning to the preferred embodiment shown in FIG. 3, mainframe computer 110 transfers visual image data along a separate display bus 130. Display bus 130 is connected to memory module 112, display device 114 and workstation 118. A separate bus is used because of the high bandwidth data transfers that must be dedicated to any high-resolution three-dimensional display function. As shown in FIG. 3, display device 114 is a large monitor such as a liquid crystal light valve (LCLV) projector, high definition television (HDTV), or other display device. In a preferred embodiment, display device 114 is a large screen of about 6 by 8 feet in dimension that substantially covers the patient's field of view. In other embodiments, display device 114 can be a head-mounted virtual display, 180 degree "bubble dome" surrounding the patient upon which the display is projected by multiple projectors, etc. Many possible display devices are suitable for use in conjunction with the present invention.

Memory module 112 is used to save the state of the session so that the patient may stop in the middle of a session and resume from the stopping point at a later time. Mainframe computer 110 transmits display data information to workstation 118. Workstation 118 is used to monitor and control the progress of the patient's session. Workstation 118 includes a display so that a supervisor operating the workstation can see an image of what the patient is viewing at any given time. A camera is also used to allow the supervisor to see the patient's face during the session to allow further monitoring of the patient. The supervisor and patient can be in voice contact with each other through the use of microphones and speakers so that communication during the session is possible.

Biometric identification 108 receives input from sensor 116. In a preferred embodiment, biometric identification 108 and sensor 116 are used to capture the image of a patient's retina for validation against a previously stored retinal "fingerprint" so that a patient will not be shown another patient's medical data. The biometric identification is a critical form of security and protection to the patient since it could be catastrophic if a patient were shown another patient's ailment as if it were their own. Naturally, other security and validation measures such as using a typed-in sign-on and password, voice recognition, or verification by the supervisor that the scan data is the patient's, etc., may be used.

In addition to security and protection, it is important that the patient believes that what they are viewing is their own body. The goal is to reinforce the belief in the patient that they can see and act upon whatever the mechanism is that is causing their disease. This is the reason for using the patient's actual scan data rather than some generic set of scan data upon which the ailment can be simulated. Nuances of a patient's anatomy, e.g., past injuries, bone structure, etc., will reinforce the patient's belief that they are viewing their own body. Aside from identifiable internal characteristics, the patient's pure and simple belief that they are viewing their own internal anatomy as faithfully reproduced by the scan data is a very strong emotional motivator that can be used to stimulate the PNI response.

Notwithstanding the above discussion, the system can be used to create simulations of ailments to instruct the patient in the initial use of the system, or for other purposes. Although the system is designed for patient use, other uses of the system are possible such as a medical school use where students can familiarize themselves with general internal anatomy in a unique and memory-reinforcing way. Also, a physician may choose to experience the visual effect of seeing a patient's disease in the intensified sensory manner that the system provides.

Input device 120 is used to accept signals from the patient, or "user," of the system so that the patient can control their visual movement through their scan data or internal anatomy. Input device 120 is also used to allow the patient to select and use different visual "tools" or weapons to fight their disease. The use of a tool causes a change in the visual presentation of the ailment so that the patient sees the ailment being diminished in strength and, eventually, completely eliminated. By having this visual reinforcement, the patient, especially a child, will be given hope and encouragement. This positive mental reaction has been shown to have a beneficial effect on the patient's immune system. (See, e.g., "Psychoneuroimmunology," 2d Edition, R. Ader, D. L. Felten, and N. Cohen, Academic Press, Inc., 1991.) Moreover, the ability of the patient to participate in their treatment to some degree by using the system of FIG. 3 reduces or eliminates the feelings of helplessness and despair that have been shown to create detrimental effects on a patient's recovery. (Id.) The specific tools and animations are discussed in more detail below.

Input device 120 may be one of many types of devices. For example, a simple joystick can be used to allow the patient to direct the viewpoint to create a "fly-through" of the patient's body much as if the patient were in an airplane. Less motor-oriented input devices such as a keyboard or mouse are less desirable because they detract from the patient's attention and physical Connection with the visual experience of viewing their internal anatomy and, especially, of viewing and acting upon their ailment. More advanced input devices such as a data glove that the patient wears around their hand will allow the patient to give input signals to the system by, for example, merely pointing or making other hand gestures. Additional controls for activating the tools/weapons discussed below may be provided to the patient, such as buttons for firing a laser or launching a missile, much like today's popular computer games.

Display and Audio Processing

Mainframe computer 110 of FIG. 3 includes software to perform the various tasks associated with display processing. The preferred embodiment will use software similar to that developed at the University of North Carolina at Chapel Hill (also referred to as "ISee") running on hardware manufactured by Silicon Graphics, Inc., and known as RealityEngine based computers. The ISee software uses the parallel processing capability of the RealityEngine hardware to perform high resolution three dimensional texture mapping and volume rendering in real time. The ISee software operates on polygon data and performs three dimensional volumetric rendering. In order to obtain the polygon data, a translation from the medical scan data generated by instrument 102 is performed by additional software in mainframe 110.

Additional software executing on mainframe 110 includes software for receiving the input signals from the patient input device, transforming the input signals into parameters for viewing position and transformation algorithms, determining new views for the image data based on the new viewing position or transformation, and displaying a new frame of images according to the new view.

In performing the audio functions described above in connection with FIG. 3, the invention utilizes three-dimensional audio spatialization sound processing. Such sound processing uses phase information and digital signal processing to give the listener the sensation that a sound is coming from a particular point in space relative to the listener. As will be apparent, any manner of audio and visual effects or processing will be adaptable for use with the present invention.

One aspect of the display processing provides for "color tagging" to mark an area of interest in the patient's anatomy. This may be necessary since the scan data may not provide a easy distinction between objects of interest in the patient's body. Other graphical aids to the patient, such as leading the patient to a diseased site, color coding for beneficial organisms versus harmful organisms, etc., may be employed.

Biofeedback Motivators

The present invention includes software to provide for "biofeedback motivation" of the patient. This involves adjusting the speed of the simulation depending on the patient's excitement or tension. In the preferred embodiment, sensing of the patient's excitement or tension during a session is done solely by the microphones built into the patient enclosure. By detecting heart pulse rate and breathing, inferences are made as to the patient's level of relaxation. Steady breathing and normal pulse rate indicate that the simulation can proceed at normal or top speeds. On the other hand, increased breathing and faster pulse rate will cause the simulation to slow down until the patient becomes relaxed, again. In other embodiments, biofeedback sensors such as electroencephalogram (EEG) sensors to monitor alpha waves or other brain waves, galvanic skin response, pulse rate, blood pressure, etc., could be used on or near the patient's body. The signals from the sensors are sent to software executing on a computer within system 100 of FIG. 3. For example, the signals could be sent to mainframe 110 where software within the mainframe performs the biofeedback motivator function.

The biofeedback motivator software adjusts the speed of movement of the patient through the body. Some other parameter of the patient's session within the system could also be adjusted, instead, according to the signals from the biofeedback sensors. Thus, if the patient becomes excited, tense, or unfocused, the speed of the viewing presentation is slowed down to attempt to cause the patient to relax. If the biofeedback sensors indicate that the patient is sufficiently relaxed then the viewing presentation proceeds at a normal rate. This ensures that the patient is receiving the full benefit of the viewing experience so that the PNI response will be heightened.

Chronotherapy

An aspect of the invention related to the timing of the patient's sessions, or viewing experiences, is called "chronotherapy." Chronotherapy requires that the patient's use of the system be timed according to the patient's natural biological rhythms. For example, if the patient is suffering from a lack of white blood cell production and it is known that white blood cell production occurs optimally at fixed times relative to the 24-hour daily cycle then the patient's use of the system of the present invention is made to occur at those optimal times. This is desirable so that the enhanced PNI response can work with, rather than against, the body's natural biological immunological responses.

Method of the Invention

Next the invention is presented as a method for stimulating a beneficial response in a patient.

Figure 4:
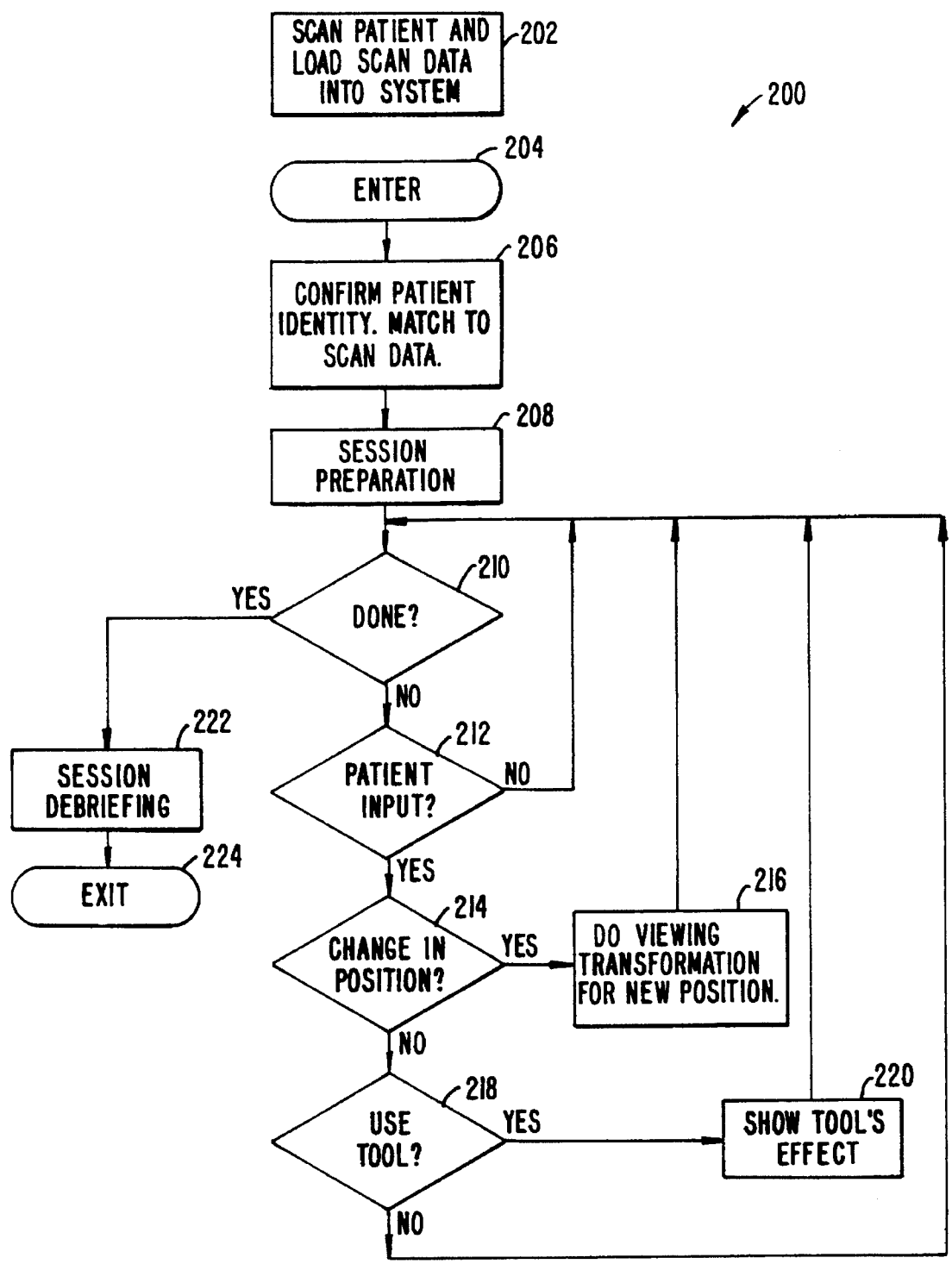
FIG. 4 illustrates a flowchart showing steps in a session of the present invention.

Using the hardware and software described above in connection with FIGS. 1–3, the present invention achieves a beneficial response in a patient in accordance with the steps illustrated in the flowchart of FIG. 4. In the following discussion, reference is made to items in both FIGS. 3 and 4.

FIG. 4 illustrates flowchart 200 showing steps in a session of the present invention. Flowchart 200 includes steps that are performed physically by the patient, or other humans, automatically by a mechanical apparatus or electronically by machines such as computers executing software in order to accomplish some of the steps, as discussed.

In general, where the flowcharts in this specification illustrate steps performed by a computer, the steps are performed by software routines executing in the computer. The routines may be implemented by any means as is known in the art. For example, any number of computer programming languages, such as "C" Pascal FORTRAN assembly language, etc., may be used. Further, various programming approaches such as procedural, object oriented or artificial intelligence techniques may be employed.

The steps of the flowcharts may be implemented by one or more software routines, processes, subroutines, modules, etc. It will be apparent that each flowchart is illustrative of merely the broad logical flow of the method of the present invention and that steps may be added to, or taken away from, the flowcharts without departing from the scope of the invention. Further, the order of execution of steps in the flowcharts may be changed without departing from the scope of the invention. Additional considerations in implementing the method described by the flowchart in software may dictate changes in the selection and order of steps. Some considerations are event handling by interrupt driven, polled, or other schemes. A multiprocessing or multitasking environment could allow steps to be executed "concurrently."

At some time prior to beginning a session the patient is scanned by an instrument such as a CAT, PET, etc., device and the scan data is loaded into the system. This step of scanning the patient and loading the scan data into the system as shown as step 202 of flowchart 200.

A patient's session begins at step 204. First, step 206 is performed to confirm that the patient's identity matches the scan data previously loaded into the system at step 202. This step is typically performed using biometric identification 108 and sensor 116 shown in FIG. 3. However, any way to confirm the patient's identity and determine the patient's scan data is acceptable.

Next, the patient is prepared for the session and is introduced into the session at step 208. Step 208 includes three discrete sequences. A first sequence is an acclimating sequence where the patient sits quietly in the patient enclosure 122 and views relaxing images and hears soothing sounds. Examples of this sequence could be stars or an evening meadow scene displayed on display device 114 while the patient hears the sound of crickets or other sounds through speakers such as speaker 124.

A second sequence shows the patient flying over a cityscape. The sequence occurs at night so the patient sees lights from a distance representing the city. The patient is not in control of the flight but is merely an observer at this stage. The patient hears a slight sound of rushing air and may also hear their breathing and heartbeat enhanced and amplified as discussed above. The third sequence has the patient flying into a pyramid within which is the patient's body. This is accomplished by using an image of the patient's face mapped onto the head of the body. The body may be displayed draped in a white sheet so that the patient can only see the facial characteristics. The patient is allowed to chose an entry point into the body and at this point takes control of the session.

Next, step 210 is executed to check whether a session should end. Since we are just starting a session, the session is not over and step 212 is the next step executed. At step 212 a check is made for input from the patient. If there is no patient input step 210 is again performed. It should be appreciated that there are many functions being performed by the system of the present invention beyond those steps shown in flowchart 200. For example, maintaining the high resolution display, monitoring the patient's heartbeat, processing and outputting the audio, operating the supervisor work station, and many other functions are ongoing functions performed by the system. For ease of discussion flowchart 200 of FIG. 4 does not show these steps but focuses on system responses to, and processing of, patient inputs.

Assuming that, at step 212, the patient has given some input, step 212 is executed to check whether the patient's input is to specify a change in position. If so, step 216 is executed where the computer system, such as computer 110 of FIG. 3, performs viewing transformations, rendering, texture mapping and other graphics operations to produce a view relating to the new position. Many ways of implementing steps 214 and 216 are possible with current computer graphics hardware and software.

If, at step 214, the patient's input is not to specify a change in position then execution proceeds to step 218 where a check is made to determine whether the patient input is a request to use a tool. If so, step 220 is executed to show the affect of the tool upon an object on the screen. For example, the tool may be a laser beam or biological "weapon" to burn away cancerous cells shown on the tissue lining of one of the patient's organs. The tools, or weapons, and their effects are discussed below in connection with FIGS. 5–7.

Whether or not steps 212, 214 and 218 result in an action based on a patient's input, execution eventually returns back to step 210 so that the loop of steps 210–220 is continuously executed until the session is terminated. A session can be terminated by the patient's request, by the supervisor's request, or by other factors such as a time limit.

Assuming, at step 210, that the session is terminated, execution falls to step 222 where a session debriefing is performed. In a preferred embodiment, the patient is wheeled out while remaining in the patient enclosure and placed in a debriefing room. The patient is encouraged to relax and to go over what they have seen and done. The patient may be presented with the sounds of the ocean, rainforest, waterfall or other soothing sounds. It may be an advantage to have the patient fall asleep at this point to enhance the effects of the PNI response. Finally, the method of the invention is exited at step 224.

User Interface

Next, FIGS. 5–7 will be discussed to present features of the graphical user interface (GUI) of the present invention.

Figure 5:
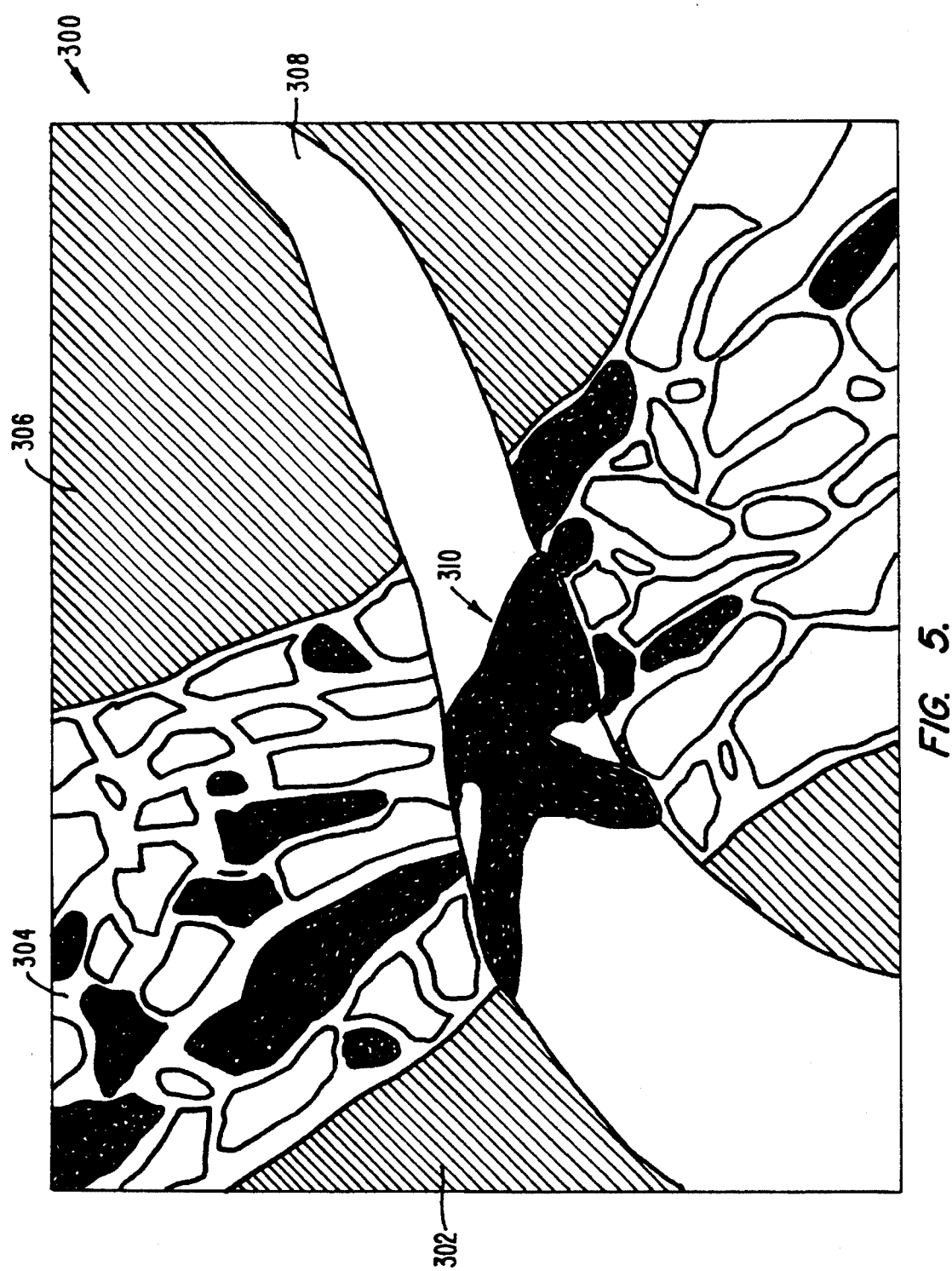
FIG. 5 shows a first screen display from a simulated patient session.

FIG. 5 shows screen display 300 from a simulated patient session using the system and method of the present invention. Screen display 300 may appear on a CRT monitor, HDTV, head-mounted display, or any other suitable display device. Note that screen displays shown in FIGS. 5–7 are conceptual, hand-drawn illustrations. The actual displays are of high resolution, include color, and are animated. It will be apparent that the discussion in connection with FIGS. 5–7 is merely illustrative of many types of displays that can be generated by the present invention.

Screen display 300 shows background tissue at 302, 304 and 306. Capillary 308 is shown in the foreground of the screen display. A harmful growth 310 is shown attached to capillary 308. As discussed above, a patient using the present invention would arrive at the location depicted in screen display 300 after navigating through anatomy created from their own scan data. The patient may be provided with one or more joysticks to control the maneuvering of their "ship" within their body to reach the site where a disease has manifested.

Figure 6:
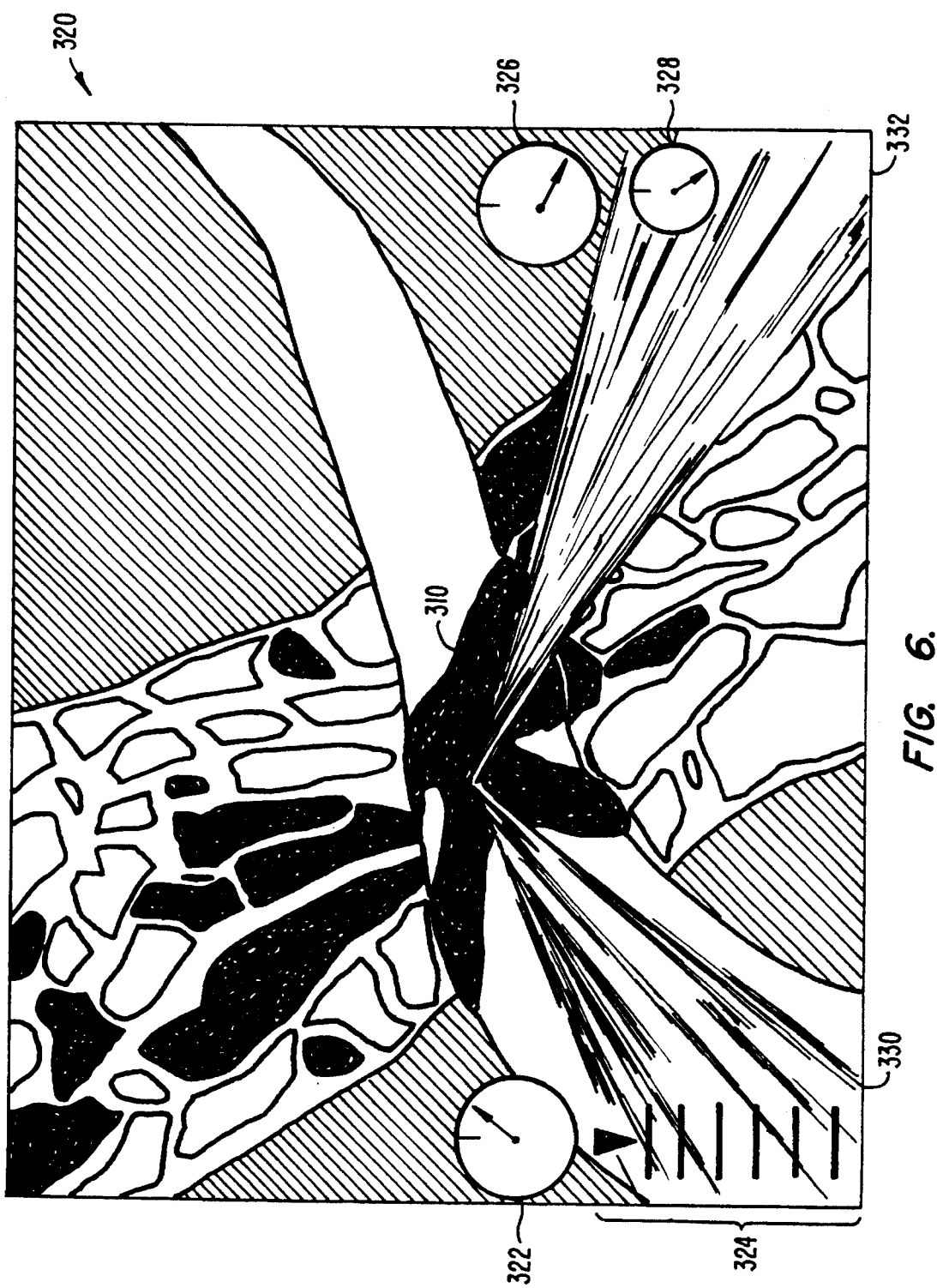
FIG. 6 shows a second screen display from a simulated patient session.

FIG. 6 shows screen display 320 including the same objects as in screen display 300, namely, the background tissue, capillary and growth. Screen display 320 also includes visual elements such as indicators and weapons of the session's virtual world.

For example, time indicator 322 shows the amount of time remaining in the session. This is used to give the patient a sense of purpose and to focus the patient's attention to the task at hand. Naturally, the time indicator is optional. Also, many other ways of indicating the amount of time remaining can be used. Fuel indicator 326 shows the amount of simulated "fuel" left. This aspect of the session can be used to encourage a patient to become engrossed in the session and to be efficient and purposeful in their movement and actions within the session's virtual world. Indicators such as time indicator 322 and fuel indicator 326 are important in creating a focused and enjoyable session, especially where children are the patients.

Heart rate indicator 328 shows the patient's heart rate. Other body conditions can be shown by additional indicators. Heart rate indicator 328 is based on sensors used by the system of the present invention to monitor the patient, as discussed above. Weapon systems indicators at 324 show various aspects of weapons, or tools, such as the type and amount of weapons available for use by the patient.

Also shown in screen display 320 are left and right laser bursts 330 and 332, respectively. In screen display 320, the patient has selected and activated one of the available weapons, namely, the "laser weapon." In a preferred embodiment, each of the weapons or tools available to the patient resembles actual tools or treatments that are used to treat the patient's disease. For example, with the laser weapon the real-life analogy is a laser scalpel used in surgery. The effect of the laser weapon used on an object in the session mimics the effect of the laser scalpel. So, for example, the laser beam will be shown to "burn away" the offending object. This reinforces the patient's belief that what is being viewed on the screen is happening, or could happen. Especially where the patient is a young child, this basis in reality will enhance the patient's belief that they are diminishing, or can diminish, their ailment and thus help to enhance the PNI response.

In FIG. 6, the laser beams are shown emanating from a point in the very near foreground toward the undesirable growth 310 near the center of the screen. The laser beams are shown just at the point of impacting the growth 310.

Figure 7:
FIG. 7 is a composite screen display to show several different aspects of the present invention's user interface.

FIG. 7 is a composite picture intended to show several different aspects of the present invention's user interface. In FIG. 7, screen display 340 shows growth 310 shortly after the laser weapon discussed above in connection with FIG. 6 has been used on it. Thus, growth 310 has a portion 342 missing from it. In the preferred embodiment, the removal of the missing section is shown in an animation such as an with an explosion, burning away or evaporating of the growth 310. Other types of "beam" weapons are "biomed fazers" which, instead of light, are composed of chemicals. The chemicals portrayed in the biomed fazer beam should be the same types of chemicals that are used in the actual treatment of the patient's disease.

FIG. 7 shows several other types of weapons at the patient's disposal. For example, a plasmocyte mine 344 is shown as a donut shape with tendrils around its outer circumference. The patient releases the plasmocyte mines in the direction of an offending object such as growth 310. The plasmocyte mines will be shown falling or flying through space toward the intended target. Once a tendril on the plasmocyte mine touches the target, the mine "explodes" to release antibodies all over the targeted object. The antibodies attack the targeted object and cause it to deteriorate.

Weapons such as the plasmocyte mines are also useful where the undesired objects are, themselves, moving throughout a part of the patient's displayed anatomy. For example, where the unwanted objects are viruses, many plasmocyte mines can be released in the path of the viruses. When a virus contacts a tendril, antibodies will be released in an animated explosion and shown to attack the virus. During the application of weapons to diseases, the patient will have to make strategic decisions similar to those in computer game playing. These thought processes encouraged in the patient will draw the patient into the task at hand and cause the patient to concentrate on, and become attuned to, their disease, their treatment, and their body's reaction to the disease and treatment. The effects of the patient's concentration will be to increase the PNI effect. At the least, the patient will obtain comfort in the imagery of seeing their diseases defeated in a realistic way based on actual scan data of their own body.

Another type of weapon, or defense, is grid filter 346. Grid filter 346 is shown inserted into capillary 308 by a cut-away view of the capillary. The patient determines where to place the filters so that blood can be purified. Any unwanted organisms or materials in the blood are removed as the blood is purified. Grid filter 346 will be shown to only let beneficial blood and materials through and will dissolve (or "zap") harmful impurities or other organisms in the blood.

A tear drop of specific chemicals is shown as a bio-bomb 350. The bio-bombs are released by the patient toward an intended target such as growth 310. Bio-bombs have a clear outer skin and contain chemicals or organisms specific to the patient's treatment. Examples of what a bio-bomb may contain are chemicals used in chemo-therapy that attach to and "eat" away a cancerous tumor, radiation elements that burn away a tumor layer by layer upon contact, cryogenic ice crystals that freeze and disintegrate an undesirable object, T-Lymphocyte cells, macrophage missiles, porphyrin pods, etc. Each item contained in a bio-bomb has its own unique characteristics so that it looks different from other items. Also, the effect of the items on the target varies along with the real-life characteristics of the corresponding chemicals or bio-organisms used in the patient's treatment. Of course, the patient can also be provided with weapons that do not have a direct bearing on their treatment.

At area 346 in capillary 308 the effect of a "mental tourniquet" is shown. By designating an area of capillary 308 and selecting the tourniquet as the weapon, the patient can cause a constricting in the capillary, or other part of the patient's displayed anatomy, to restrict blood flow to an undesirable object that requires blood to sustain itself. Another type of weapon/tool is a "suffocation web" (not shown). This is a transparent film that is directed by the patient to attach itself over an undesired object. The suffocation web prevents the object from receiving oxygen and the object will be shown to wither and die away.

Many other weapons and tools are possible. Some patients may prefer non-violent tools such as crystals, "healing hands," wands, light, etc.

Thus, it has been shown that the patient may apply several different weapons to undesirable objects displayed within the patient's anatomy. By presenting the patient with a visual picture and a virtual experience, and by taking the patient through the motions of locating, moving to, and purging their system of these undesirable objects in a way that links, by visual metaphors, what the patient is seeing and doing in the session to what the patient is experiencing with their physical ailment, the patient's PNI response is stimulated.

In the foregoing specification, the invention has been described with reference to a specific exemplary embodiment thereof. It will, however, be evident that various modifications and changes may be made without departing from the broader spirit and scope of the invention as set forth in the appended claims. For example, various programming languages and techniques can be used to implement the disclosed invention. Also, the specific logic presented to accomplish tasks within the present invention may be modified without departing from the scope of the invention. Many such changes or modifications will be readily apparent to one of ordinary skill in the art. The specification and drawings are, accordingly, to be regarded in an illustrative rather than a restrictive sense, the invention being limited only by the provided claims.

What is claimed is:

1. A method of interactive simulation of a reduction in an ailment-causing agent in a patient having an ailment, comprising the steps of:

inputing medical scan data representative of the patient's anatomy into a computer memory storage device, the medical scan data including an indication of the ailment-causing agent;

reading a portion of the medical scan data from the computer memory storage device;

displaying the portion of the medical scan data on a display device visible to the patient, the portion displayed being a view of the ailment-causing agent;

accepting signals from a user input device controlled by the patient, wherein the signals describe the patient's manipulation of the user input device to effect a simulated attack on the display of the ailment-causing agent; and displaying a modified view of the ailment-causing agent, the modified view being a view modified by the simulated effects of the simulated attack.

2. The method of claim 1, further comprising a step of prompting the patient to manipulate the user input devices to simulate an attack on the display of the ailment-causing agent, the step of prompting being performed before the step of accepting signals from the user input device.

3. The method of claim 2, further comprising a step of biofeedback wherein the patient's neurological system responds to the simulation of the reduction of the ailment-causing agent as if the actual ailment-causing agent shown in the view of the ailment-causing agent was attacked or reduced.

4. The method of claim 1, wherein the step of displaying the portion of medical scan data and the step of displaying a modified view are steps performed at times determined by a biological rhythm of the patient.

5. The method of claim 1, wherein the step of displaying a portion of the medical scan data is a step of displaying an animated view of the medical scan data and the step of displaying an modified view is a step of displaying an animated view of the ailment-causing agent being reduced over time.

6. The method of claim 5, further comprising a step of displaying beneficial objects of the patient's anatomy or simulations of agents to be added to the patient's anatomy, and wherein the step of displaying a modified view comprises a substep of displaying an animated sequence showing an increase in the number of beneficial objects in the patient's anatomy.

7. The method of claim 1, further comprising a step of displaying a reduction in a nutritive source for the ailment-causing agent.

8. The method of claim 1, further comprising a step of displaying an entry simulation which simulates the patent's entry into the patient's body using the medical scan data.

9. The method of claim 1, further including the steps of:

sensing the patient's stress level using at least one sensor; and adjusting the displaying steps according to results of the step of sensing the patient's stress level.

10. The method of claim 1, further comprising the steps of:

pausing before each of the displaying steps; and adjusting an animation speed of an animated display.

11. The method of claim 1, further comprising a step of scanning the patient to obtain the medical scan data, wherein the step of scanning is performed before the step of inputing medical scan data representative of the patient's anatomy.

12. The method of claim 11, wherein the step of scanning the patient is a step of performing a computer-aided tomography (CAT) scan.

13. The method of claim 11, wherein the step of scanning the patient is a step of performing a magnetic resonance imagery (MRI) scan.

14. The method of claim 11, wherein the step of scanning the patient is a step of performing a positron emission tomography (PET) scan.

15. A interactive computer system for simulating a reduction in an ailment-causing agent in a patient having an ailment and for simulating effects of the patient's actions attacking the ailment-causing agent, the apparatus comprising:

a computing system;

a user input device coupled to the computing system;

a graphical display device, visible to the patient, coupled to the computing system;

data storage for medical scan data, coupled to the computing system, wherein medical scan data obtained from the patient's anatomy including scan data of an ailment-causing agent is stored; and a program memory, coupled to the computing system, configured to control the computing system to accept inputs from the patient and control the graphical display device to display at least a portion of the medical scan data showing the ailment-causing agent, the program memory further comprising programming instructions to accept user inputs representing a simulated attack on the ailment-causing agent and programming instructions to effect a display of the displayed portion of the medical scan data as modified by the user inputs representing the simulated attack.

16. The interactive computer system of claim 15, further comprising means for entry of medical scan data from a scanning device to the data storage.

* * * * *